US008623864B2

(12) United States Patent
Christensen et al.

(10) Patent No.: US 8,623,864 B2
(45) Date of Patent: Jan. 7, 2014

(54) THIORIDAZINE AND DERIVATIVES THEREOF FOR REVERSING ANTI-MICROBIAL DRUG-RESISTANCE

(75) Inventors: Jørn B. Christensen, Virum (DK); Oliver Hendricks, Gråsten (DK); Jette Kristiansen, Egernsund (DK)

(73) Assignee: NOA Sic Aps, Egernsund ( * ) Notice: Subject to any disclaimer, the term of this patent is extended or adjusted under 35 U.S.C. 154(b) by 694 days.

(21) Appl. No.: 10/579,112

(22) PCT Filed: Nov. 15, 2004

(86) PCT No.: PCT/IB2004/003730

§ 371 (c)(1),
(2), (4) Date: Feb. 28, 2007

(87) PCT Pub. No.: WO2005/046694

PCT Pub. Date: May 26, 2005

(65) Prior Publication Data

US 2007/0287702 A1    Dec. 13, 2007

(30) Foreign Application Priority Data

Nov. 13, 2003    (DK) ................................ 2003 01690

(51) Int. Cl.
*A61K 31/54*    (2006.01)

(52) U.S. Cl.
USPC ....................................................... 514/225.5

(58) Field of Classification Search
USPC ....................................................... 514/225.5
See application file for complete search history.

(56) References Cited

FOREIGN PATENT DOCUMENTS

| EP | 1 689 405 B1 | 9/2001 |
| GB | 873316 | 7/1961 |
| WO | WO 02/22130 A2 | 3/2002 |
| WO | WO 02/057244 A1 | 7/2002 |
| WO | WO 02/058684 A2 | 8/2002 |
| WO | WO 02/089810 A1 | 11/2002 |
| WO | WO 03/062388 A2 | 7/2003 |

OTHER PUBLICATIONS

Dorwald FA, Preface "Side Reactions in Organic Synthesis" 2005, Wiley-VCH, Weinheim, p. IX.*
Baldessarini RJ and Tarazi FI, Chapter 20 Drugs and the Treatment of Psychiatric Disorders—Psychosis and Mania, "Goodman & Gilman's The Pharmacological Basis of Therapeutics, 10th ed." Hardman JG, Limbird LE, and Gilman AG, Eds., McGraw-Hill, 2001, 485-520 (pp. 485 and 487 provided).*
Viveiros M, Amaral L. Enhancement of antibiotic activity against poly-drug resistant *Mycobacterium tuberculosis* by phenothiazines. Int J Antimicrob Agents. Mar. 2001;17(3):225-8.*
Froimowitz, M., et al., "Biologically Active Conformers of Phenothiazines and Thioxanthenes. Further Evidence for a Ligand Model of Dopamine D2 Receptor Antagonists," Jan. 15, 1993, American Chemical Society, J. Med. Chem, 36, pp. 2219-2227.
Glass-Marmor, L., et al., "Calmodulin antagonists decrease glucose 1,6-bisphosphate, fructose 1,6-bisphosphate, ATP and viability of melanoma cells," European Journal of Pharmacology 313, 1996, pp. 265-271.
Jortani, Saeed A., et al., "Determination of Thioridazine Enantiomers in Human Serum by Sequential Achiral and Chiral High-Performance Liquid Chromatography," Journal of Analytical Toxicology, vol. 17, Oct. 1993, pp. 374-377.
Kristiansen, Malthe M., et al., "Phenothiazines alter resistance of methicillin-resistant strains of *Staphylococcus aureaus* (MRSA) to oxacillin in vitro," International Journal of Antimicrobial Agents 22, 2003, pp. 250-253.
Kristiansen, J.E., "Non-Antibiotics: What are they and what can they be used for?" Satellite Meeting Abstract, SA-1, p. 620.
Kaatz, Glenn W., et al., "Phenothiazines and Thioxanthenes Inhibit Multidrug Efflux Pump Activity in *Staphylococcus aureus*," Antimicrobial Agents and Chemotherapy, Feb. 2003, 47, p. 719-726.
Ordway, D., et al., "Clinical Concentrations of Thioridazine Kill Intracellular Multidrug-Resistant *Mycobacterium tuberculosis*," Antimicrobial Agents and Chemotherapy, Mar. 2003, 47, pp. 917-922.
Patrick, Kennerly S., et al., "Relative Configuration of Thioridazine Enantiomers," Chirality 3:208-211, 1991.
Radhakrishnan, V., "Potentiality of tricyclic compound thioridazine as an effective antibacterial and antiplasmid agent," Indian Journal of Experimental Biology, vol. 37, Jul. 1999, pp. 671-675.
Ramu, A., et al., "Reversal of multidrug resistance by phenothiazines and structurally related compounds," Cancer Chemotherapy and Pharmacology, 1992, 30, pp. 165-173.
Svendsen, C.N., et al., "Concentration and Distribution of Thioridazine and Metabolites in Schizophrenic Post-mortem Brain Tissue," Psychiatry Research, 23, 1988, pp. 1-10.
Svendsen, C.N., et al., "Receptor affinity, neurochemistry and behavioral characteristics of the enantiomers of thioridazine: evidence for different stereoselectivities at D1 and D2 receptors in rat brain," Neuropharmacology, 1988, 27 (11), 1117-24.
Akiyama, S., et al., "Circumvention of multiple-drug resistance in human cancer cells by thioridazine, trifluoperazine, and chlorpromazine," JNCI, Journal of the National Cancer Institute, 1986.
De Gaitani, C.M., et al., "Racemization and degradation of thioridazine and thioridazine 2-sulfone in human plasma and aqueous solutions," Chirality, 2003, 15 (6), 479-485.
Eap, C.B., et al., "Determination of the enantiomers of thioridazine, thioridazine 2-sulfone, and of the isomeric pairs of thioridazine 2-sulfoxide and thioridazine 5-sulfoxide in human plasma," Journal of Chromatography, B: Biomedical Applications, 1995, 669 (2), 271-9.
J. Molnar et al., The antibacterial action and R-factor-inhibiting activity by chlorpromazine (1976) vol. 31, pp. 444-445.
Mortensen et al., The antimicrobial effect of some neuroleptics on strains isolated from patients with meningitis. Pharmacology and Toxicology (1992), vol. 71, 449-451.
Svendsen CN et al.: Receptor affinity, neurochemistry and behavioral characteristics of the enantionmeres of thioridazine: evidence for different stereoselectivities at D1 and D3 receptors in rat brain. Neuropharmacology (1988), 27 (11): 1117-1124.

* cited by examiner

*Primary Examiner* — Paul Zarek
(74) *Attorney, Agent, or Firm* — Merchant & Gould P.C.

(57) ABSTRACT

The present invention relates to compositions comprising thioridazine, and derivatives thereof, together with antibacterials. These compositions have been found greatly enhance the activity of many classes of antibacterials, allowing the antibacterials to be administered at significantly lower doses. The thioridazine and the antibacterial act synergistically by pacifying the bacteria to the antibacterials. This synergistic affect lowering the inhibitory or effective concentration of the antimicrobials is most pronounced with the levorotatory isomer of thioridazine compared to the racemic or dextrorotatory isomer.

13 Claims, No Drawings

THIORIDAZINE AND DERIVATIVES THEREOF FOR REVERSING ANTI-MICROBIAL DRUG-RESISTANCE

This application claims benefit of Danish patent application no PA 2003 01690, filed Nov. 13, 2003, as well as international application no PCT/IB04/03730, filed Nov. 15, 2004, which applications are incorporated herein by reference. A claim of priority to the extent appropriate is made.

FIELD OF THE INVENTION

Thioridazine, and derivatives thereof, have been found greatly enhance the activity of many classes of antibacterials, allowing the antibacterials to be administered at significantly lower doses. The current understanding is that thioridazine acts by impeding the drug resistance mechanisms of the bacterial cell lines, such that the bacteria do not resist the antibacterials. The thioridazine and the antibacterial act synergistically by pacifying the bacteria to the antibacterials. This synergistic affect lowering the inhibitory or effective concentration of the antimicrobials is most pronounced with the levorotatory isomer of thioridazine compared to the racemic or dextrorotatory isomer.

BACKGROUND OF THE INVENTION

Drug-resistant infectious agents—those that are not efficiently killed or substantially growth-inhibited by antimicrobial compounds—are an increasingly important public health concern. Tuberculosis, gonorrhea, malaria and childhood ear infections are examples of diseases which have become more difficult to treat due to the emergence of drug-resistant pathogens. Antimicrobial resistance is becoming a factor in virtually all hospital-acquired (nosocomial) infections. It has been estimated that the annual cost of treating antibiotic resistant infections in the United States alone may be as high as $30 billion.

Antimicrobial resistance has been recognized since the introduction of penicillin nearly 50 years ago, when penicillin-resistant infections caused by *Staphylococcus aureus* rapidly appeared. Strains of *Staphylococcus aureus* resistant to methicillin and other antibiotics are endemic in hospitals. Infection with methicillin-resistant *S. aureus* (MRSA) strains may also be increasing in non-hospital settings. A limited number of drugs remain effective against these infections. However, *S. aureus* strains with reduced susceptibility to vancomycin have emerged recently in Japan and the United States. Strains of multidrug-resistant tuberculosis (MDR-TB) have emerged over the last decade and pose a particular threat to people infected with HIV. Drug-resistant strains are as contagious as those that are susceptible to drugs. Diarrheal diseases cause almost 3 million deaths a year—mostly in developing countries, where resistant strains of highly pathogenic bacteria such as *Shigella dysenteriae, Campylobacter, Vibrio cholerae, Escherichia coli* and *Salmonella* are emerging.

Given the escalating problems associated with poorly treatable infections caused by an increasing variety of resistant infectious agents, such as antibiotic-resistant bacteria, there is a great need for improved anti-microbial treatments. The two major avenues for research into such treatments are development of novel antimicrobial compounds and the development of agents which serve to reverse the resistance displayed by the pathogens. The current invention relates to compounds useful for reversing drug resistance and thus improving therapeutic treatment of infections associated with resistant pathogens.

Certain CNS drugs have beneficial effects on infections, either via inherent antibiotic properties, or via reversal of resistance to classical antibiotics. The use of members of the phenothiazine class of CNS drugs for reversal of multidrug resistance (MDR) is known in the art (Ramu et al. *Cancer Chemother. Pharmacol.* 1992, 30, 165). Among the phenothiazines, thioridazine has been reported to be effective in reversing resistance to a variety of antineoplastic agents in tumour cell lines (Akiyama et al. *JNCI* 1986, 76, 839). It has been suggested that the mechanism of action of thioridazine in such cell lines involves inhibition of drug efflux.

Furthermore, thioridazine has been suggested as a potential antituberculosis agent, based on its ability to kill *Mycobacterium tuberculosis* in vitro (Ordway et al. *Antimicrobial Agents Chemother.* 2003, 47, 917). Bactericidal and bacteriostatic properties of thioridazine have been recorded in a large number of bacterial strains (Radhakrishnan et al. *Indian J. Exp. Biol.* 1999, 37, 671).

The neuroleptic thioridazine (Melleril) is a racemic phenothiazine. The enantiomers of thioridazine have been resolved and well characterised (Patrick et al. *Chirality* 1991, 3, 208; GB 873,316; De Gaitani et al. *Chirality* 2003, 15, 479). Metabolism, providing several active metabolites, of thioridazine has been shown to be stereoselective (Eap et al. *J. Chromatog. B: Biomed. Appl.* 1995, 669, 271; Svendsen et al. *Psychiatry Research* 1988, 23, 1). The use of thioridazine racemate for reversal of resistance has been disclosed, and a potential mode of action discussed (Kristiansen, M., *5th European Congress on Chemotherapy and Infection*, Rhodes, 2003).

The dextrorotatory (R) enantiomer of thioridazine has been ascribed more potent CNS-related activity than the racemate or levorotatory enantiomer. Recent studies have suggested that the levorotatory (S) form shows selectivity for $D_1$-receptors, while the dextrorotatory isomer has high affinity for $D_2$-receptors (Svendsen et al. *Neuropharmacol.* 1988, 27, 1117-25).

For the application of CNS-active drugs as antibacterials, such as those belonging to the phenothiazine class, it would clearly be beneficial to apply compounds with relatively low potency at e.g. dopamine receptors, but with potent antimicrobial activity, e.g. mediated via interactions with a bacterial efflux pump. Such compounds would be superior since side effects related to the neuropsychopharmacodynamic properties might be expected to be less pronounced. Thus, one advantage provided by the present invention is that lower doses of the CNS-active drugs phenothiazine antibacterials are required then presently used, leading to lesser side effects.

Thus, a benefit provided by the present invention is that a composition which comprises a the phenothiazine compounds of the invention and an anti-microbial agent, requires lower doses of the anti-microbial agent then presently used when attempting to treat infections. Thus, infections presently resistant and untreatable using a particular agent now become treatable using same agent. Furthermore, infections which required high doses of the anti-microbial agent now only need lower doses in the treatment of infections showing some resistance.

DESCRIPTION OF THE INVENTION

Given bacterial resistance to antibiotics is endemic all over the world as well as in hospitals to almost epidemic proportions, huge efforts have been invested in countering this near crisis in the medical industry. Yet the crisis since to be perpetually developing, prompting new studies into new antibiotics. The present inventors consider the strategy of developing new antibiotics to be quasi futile and instead have developed an alternative approach, as disclosed by the present invention.

As used herein, the term "antimicrobial agent" is intended to cover drugs, chemicals, or other substances that either kill or slow the growth of microbes. Among the antimicrobial agents in use today are antibacterial drugs, antiviral agents, antifungal agents, and antiparisitic drugs. Common examples of such agents include, for example, beta-lactams (penicillins and cephalosporins), semisynthetic penicillin derivatives, clavulanic acid analogues, monobactams, carboxypenems, aminoglycosides, glycopeptides, lincomycins, macrolide antibiotics, polypeptides, polyenes, rifamycins, tetracyclines, semisynthetic tetracyclines, and chloramphenicol derivatives.

Specific examples of antimicrobial agents include acyclovir, albendazole, amikacin, amphotericin B, aztreonam, azithromycin, caspofungin, cefepime, ceftriaxone, cefotaxime, chloramphenicol, cidofovir, clarithromycin, fluconazole, flucytosine, foscarnet, ganciclovir, imipenem, itraconazole, linezolid, meropenem, pentamidine, piperacillin-tazobactam, rifabutin, valganciclovir, vancomycin, penicillin, cephalosporin, griseofulvin, bacitracin, polymyxin B, erythromycin, neomycin, streptomycin, tetracycline, gentamicin, rifamycin, penicillin G, cephalothin, ampicillin, amoxycillin, clavamox, aztreonam, imipenem, streptomycin, gentamicin, clindamycin, polymyxin, bacitracin, amphotericin, nystatin, rifampicin, oxacillin and doxycycline.

The terms "antimicrobial resistance" and "resistance" are used interchangeably to describe a situation where a pathogenic microbe has undergone some sort of change that reduces or eliminates the effectiveness of drugs, chemicals, or other agents to cure or prevent infections.

The terms "microbes" is used in its common meaning, i.e. to cover pathogenic organisms so small that a microscope is required to see them. Microbes are also called microorganisms, and include bacteria, viruses, fungi, and parasites, out of which the former two, especially bacteria are the most relevant for the purposes of the present invention.

The term "$C_{1-6}$-alkyl" should be understood to designate linear or branched alkyl groups comprising from 1 to 6 carbon atoms. Representative examples include methyl, ethyl, propyl, isopropyl, butyl, sec-butyl, tert-butyl, pentyl isopentyl, hexyl, methylpentyl, and neopentyl.

The term "$C_{3-8}$-cycloalkyl" designates cyclic alkyl groups comprising from 3 to 8 carbon atoms, such as cyclopropyl, cyclobutyl, cyclopentyl, cyclohexyl, cyclopropylmethyl, cyclopentylethyl, methylcyclopropyl, dimethylcyclobutyl, ethylcyclopropylethyl, and the like.

The term "aryl" is intended to designate optionally substituted carbacyclic aromatic moieties, which may be isolated or fused, such as phenyl and anthryl.

The term "heteroaryl" should be understood to cover optionally substituted aromatic moieties comprising one or more heteroatoms independently selected from N, O, and S. Heteroaryl groups may further be fused to one or more heteroaryl or aryl rings so as to include bicyclic and polycyclic ring systems. The heteroaryl groups may be connected either via a heteroatom, or via a carbon atom. Preferred heteroaryl groups are those comprising the aromatic sextet, i.e. 6 pi-electrons in the ring system, and those bicyclic systems which have 10 pi-electrons; Typical examples include furyl, thienyl, pyrrolyl, indolyl, pyridyl, benzofuryl, benzothienyl, pyrazolyl, diazolyl, oxazolyl, thiazolyl, oxadiazolyl, thiadiazolyl, triazolyl, tetrazolyl, imidazolyl, benzoimidazolyl, benzoxazolyl, indazolyl, and the like.

"Arylalkyl" designates an aryl group connected through a $C_1-C_6$ alkylene tether such as methylene, ethylene, propylene, tetramethylene, pentamethylene, or hexamethylene.

"Heteroarylalkyl" similarly designates a heteroaryl group connected through a $C_1-C_6$ alkylene tether such as methylene, ethylene, propylene, tetramethylene, pentamethylene, or hexamethylene.

Substituents presented as "CO—$C_{1-6}$-alkyl", "CO—$C_{3-8}$-cycloalkyl", "COO—$C_{1-6}$-alkyl", "COO—$C_{3-8}$-cycloalkyl", "CO-aryl", "CO-heteroaryl", "COO-aryl", "COO-heteroaryl", "arylalkyl-CO", "heteroarylalkyl-CO", "arylalkyl-OOC" and "heteroarylalkyl-OOC" should be understood as connected through carbonyl (CO) or carboxy (COO) tethers respectively, i.e. designating ketone, ester or amide (when a heteroaryl group is connected via a nitrogen atom) appendages. It follows that these groups give rise to amide, urea or carbamate functionalities when appended to a nitrogen atom.

The terms "arylalkyloxy" and "heteroarylalkyloxy" are intended to cover arylalkyl and heteroarylalkyl groups, respectively, which are appended, as substituents, through an oxygen atom.

The terms "aryloxy", "heteroaryloxy", "arylamino", and "heteroarylamino" are used in their usual meaning, i.e. aromatic or heteroaromatic groups connected, as substituents, through an oxygen atom or amino (NH) group, respectively.

"Halogen" includes fluorine, chlorine, bromine and iodine atoms, with the former two being generally preferred.

In the context of the present invention, the term "optionally substituted" is used to incorporate the optional presence of one or more substituents which may be selected from hydroxy, $C_{1-6}$-alkyl, $C_{1-6}$-alkoxy, $C_{2-6}$-alkenyloxy, oxo, carboxy, $C_{1-6}$-alkoxycarbonyl, $C_{1-6}$-alkylcarbonyl, formyl, aryl, arloxy, arylamino, aryloxycarbonyl, arylcarbonyl, heteroaryl, heteroarylamino, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl) amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkylsulphonyl-amino, aryl-sulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, nitro, sulphanyl, amino, amino-sulfonyl, mono- and di($C_{1-6}$-alkyl)amino-sulfonyl, dihalogen-$C_{1-4}$-alkyl, trihalogen-$C_{1-4}$-alkyl, and halogen, where aryl and heteroaryl representing substituents may be substituted 1-3 times with $C_{1-4}$-alkyl, $C_{1-4}$-alkoxy, nitro, cyano, amino or halogen, and any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidine.

Preferably, such optional substituents are selected from hydroxy, $C_{1-6}$-alkyl, $C_{1-6}$-alkoxy, carboxy, $C_{1-6}$-alkylcarbonyl, formyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, $C_{1-6}$-alkylcarbonylamino, guanidino, carbamido, $C_{1-6}$-alkyl-sulphonyl-amino, aryl-sulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, sulphanyl, amino, amino-sulfonyl, mono- and di($C_{1-6}$-alkyl)amino-sulfonyl or halogen, where any alkyl, alkoxy and the like representing substituents may be substituted with hydroxy, $C_{1-6}$-alkoxy, $C_{2-6}$-alkenyloxy, amino, mono- and di($C_{1-6}$-alkyl) amino, carboxy, $C_{1-6}$-alkylcarbonylamino, halogen, $C_{1-6}$-alkylthio, $C_{1-6}$-alkyl-sulphonyl-amino, or guanidine.

Especially preferred examples are $C_{1-6}$-alkyl, $C_{1-6}$-alkoxy, amino, mono- and di($C_{1-6}$-alkyl)amino, sulphanyl, carboxy or halogen, where any alkyl, alkoxy and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidine.

The inventors have performed detailed studies with phenothiazines such as thioridazine and its enantiomers in an attempt to define the properties of these substances in the context of reversal of drug resistance, more specifically reversal of resistance to antimicrobial agents, such as antibacterial drugs. Under certain experimental settings, racemic or enantiopure thioridazine displayed equipotent bacteriostatic or bactericidal properties when given alone or in combination with traditional antibiotics. Invariably, and surprisingly, racemic or enantiopure thioridazine acted in a syngergistic manner to lover the MIC of the other antibiotic. Even more surprisingly, however, under certain bacterial strains and/or when combined with specific antibiotic drugs, one of the enantiomers showed highly superior activity. For example, the levorotatory enantiomer was much more efficient in reversing resistance towards erythromycin in *Streptococcus* strains. Incidentally, the levorotatory enantiomer has earlier been reported to display less challenging CNS pharmacodynamic activity, e.g. weaker blockade of dopamine D2-receptors, than the dextrorotatory enantiomer. Taken together, these facts suggest that the levorotatory form of thioridazine should clearly be superior in the context of reversal of drug resistance due to potentially fewer side effects. These unprecedented findings provide a new opportunity for improved antimicrobial therapy, especially when pathogens associated with at least some degree of resistance are implicated, involving administering enantiomerically enriched thioridazine or analogs thereof, in combination with one or more antimicrobial agents. Compositions comprising non-racemic thioridazine or analogs thereof, i.e. compounds of formulae I or II, and optionally comprising one or more antimicrobial agents may provide highly effective drugs for prophylaxis or treatment of e.g. bacterial infections caused by bacteria which have been shown to possess, or may be suspected to be liable to develop, at least some resistance towards one or more antibacterial agents.

A first aspect of the invention defines a composition comprising an antimicrobial agent and a compound of the formula I

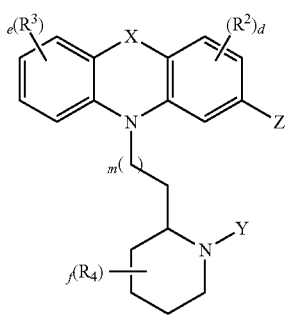

I wherein
X is selected from the group consisting of O, $NR^1$, Se, P, PO, SO and S;

Z is selected from the group consisting of $SR^5$, $SOR^5$, $SO_2R^5$, $NHR^5$, $NR^5R^5$, $NR^1R^5$, $OR^5$, $COR^5$, $COOR^5$, and $POR^5$, $PO_2R^5$, $PO_2OR^5$, and $OPO_2OR^5$;

Y is hydrogen or $C_{1-6}$-alkyl;

m is a whole number selected from the group consisting of 0, 1, 2, 3, 4, 5, and 6;

$R^1$ is selected from the group consisting of hydrogen, $C_{1-6}$-alkyl, $C_{3-8}$-cycloalkyl, aryl, heteroaryl, arylalkyl, heteroarylalkyl, CO—$C_{1-6}$-alkyl, CO—$C_{3-8}$-cycloalkyl, COO—$C_{1-6}$-alkyl, COO—$C_{3-8}$-cycloalkyl, CO-aryl, CO-heteroaryl, COO-aryl, COO-heteroaryl, arylalkyl-CO, heteroarylalkyl-CO, arylalkyl-OOC and heteroarylalkyl-OOC;

Each $R^2$ is independently selected from the group consisting of $C_{1-6}$-alkyl, halogen, $C_{3-8}$-cycloalkyl, OH, $NH_2$, $NHR_1$, $N(R_1)_2$, O—$C_{1-6}$-alkyl, O—$C_{3-8}$-cycloalkyl, NH—$C_{1-6}$-alkyl, NH—$C_{3-8}$-cycloalkyl, S—$C_{1-6}$-alkyl, S—$C_{3-8}$-cycloalkyl, aryl, heteroaryl, aryloxy, heteroaryloxy, arylamino, heteroarylamino, arylalkyl, heteroarylalkyl, arylalkyloxy and heteroarylalkyloxy;

d is selected from 0, 1, 2, and 3;

Each $R^3$ is independently selected from the group consisting of $C_{1-6}$-alkyl, halogen, $C_{3-8}$-cycloalkyl, OH, $NH_2$, $NHR_1$, $N(R_1)_2$, O—$C_{1-6}$-alkyl, O—$C_{3-8}$-cycloalkyl, NH—$C_{1-6}$-alkyl, NH—$C_{3-8}$-cycloalkyl, S—$C_{1-6}$-alkyl, S—$C_{3-8}$-cycloalkyl, aryl, heteroaryl, aryloxy, heteroaryloxy, arylamino, heteroarylamino, arylalkyl, heteroarylalkyl, arylalkyloxy and heteroarylalkyloxy;

e is selected from 0, 1, 2, 3, and 4;

Each $R^4$ is independently selected from the group consisting of $C_{1-6}$-alkyl, halogen, $C_{3-8}$-cycloalkyl, OH, O—$C_{1-6}$-alkyl, O—$C_{3-8}$-cycloalkyl, aryl, heteroaryl, aryloxy, heteroaryloxy, arylalkyl, heteroarylalkyl, arylalkyloxy and heteroarylalkyloxy;

f is selected from 0, 1, 2, 3, 4, 5, 6, 7, and 8; and $R^5$ is selected from the group consisting of hydrogen, $C_{1-6}$-alkyl, $C_{3-8}$-cycloalkyl, aryl, heteroaryl, arylalkyl, and heteroarylalkyl;

or a pharmaceutically acceptable salt of a compound of formula I and further comprising a pharmaceutically acceptable excipient or carrier.

The present inventors have found that providing a compound of formula I in a composition comprising an antimicrobial allows for the composition to comprise less than the minimum inhibitory concentration of the antimicrobial dramatically.

In a preferred embodiment of a compound of formula I, X is S. Typically, Z is selected from the group consisting of $SR^5$, $SOR^5$, $NHR^5$ and $OR^5$, more typically wherein Z is selected from the group consisting of $SR^5$, $SOR^5$, most typically, Z is $SR^5$. $R^5$ is typically a $C_{1-6}$-alkyl. Y is typically methyl.

m is typically selected from the group consisting of 0, 1, 2 and 3, preferably 1, 2 and 3, more preferably 1 and 2, most preferably 1. d is typically selected from the group consisting of 0, 1, 2 and 3, preferably 0, 1, and 2, more preferably 0 and 1. e is typically selected from the group consisting of 0, 1, 2 and 3, preferably 0, 1, and 2, more preferably 0 and 1. f is selected from the group consisting of 0, 1, 2, 3, and 4, preferably 0, 1, and 2, more preferably 0 and 1.

In a preferred embodiment of the invention, the compound of formula I is a phenothiazine derivative. From the Examples, it can be seen that using, for example 8 or 12 µg/ml of thioridazine resulted in dramatic reduction of the dose of the antibiotic to effective inhibit bacterial invasion in a number of exemplary human cell lines against a plethora of bacterial strains.

Compounds of the formula I, such as phenothiazines, have been found to reduce the inhibitory concentration of antimicrobials several fold. In a preferred embodiment of the compounds of formula I, the compound of formula I is selected from thioridazine, chlorpromazine, and prochlorperazine and salts thereof. The phenothiazine derivative may be typically selected from the group consisting of (±)-thioridazine, (+)-thioridazine, (−)-thioridazine, chlorpromazine, and perchlorperazine, and salts thereof.

As stated, phenothiazine and derivatives thereof, such as thioridazine have been found greatly enhance the activity of many classes of antibacterials, allowing the antibacterials to be administered at significantly lower doses. The current understanding, but without being bound to a particular theory is that phenothiazine acts by impeding the drug resistance mechanisms of the bacterial cell lines, such that the bacteria do not resist the antibacterials. The phenothiazine and the antibacterial act synergistically by pacifying the bacteria to the antibacterials. Together they act in a synergistic manner as bactericidal agents effectively killing the bacteria at concentrations of each of them dramatically lower the concentrations or doses required by either of them to act as bactericidal agents. Given the phenothiazine and the antibacterial actually are currently understood to perform different functions to provide the synergistic lowering of the individual doses combined to have bactericidal activity (the phenothiazine pacifies the bacteria or disables the efflux pumps and the other actually acts as the bactericidal agent), the effect may be more properly defined as a symbiotic synergism. Irrespective, it has furthermore been surprisingly found that the effect is dramatically more than additive. For instance, as can be seen from the Examples, Erythromycin has a MIC of 24 µg/ml against a known bacterial strain. The phenothiazine thioridazine, which also has bactericidal activity, has a MIC of 16 µg/ml. A combination of 12 µg/ml of thioridazine in racemic form allows for the use of less than 8 µg/ml of Erythromycin.

This synergistic affect lowering the inhibitory or effective concentration of the antimicrobials is most pronounced with the levorotatory isomer of thioridazine compared to the racemic or dextrorotatory isomer. In the same case, with 12 µg/ml of the levorotatory isomer of thioridazine, only 1 µg/ml of Erythromycin was required. Thus, an embodiment of the invention is a composition comprising Erythromycin and a phenothiazine, preferably the levorotatory isomer of thioridazine. In embodiments comprising the levorotatory enantiomer of thioridazine, the composition comprises at most 20%, preferably at most 10%, more preferably at most 5%, most preferably at most 2.5%, such as at most 1% of dextrorotatory epimer of thioridazine, or a salt thereof.

In a preferred embodiment of the invention, the composition comprises an antimicrobial agent and the formula I is the levorotatory enantiomer of thioridazine, or a salt thereof.

An even more dramatic demonstration of the synergism between phenothiazines and antimicrobials, the effective MIC of oxacillin was reduced from over 256 µg/ml (against a common bacterial strain) to 1 µg/ml when combined with 8 µg/ml of the phenothiazine thioridazine.

As stated, in one preferred embodiment, the compound of formula I is thioridazine. Thioridazine may be administered orally and may be in the form of the hydrochloride or the base. The amount of thioridazine in a dosage unit is typically less than for the amount used for the treatment of psychiatric disorders and less than the MIC of thioridazine. The usual dosage range for the treatment of the psychiatric disorders is 150-600 mg daily of thioridazine hydrochloride and administered in dosage units of 10, 25, 50 or 100 mg of thioridazine hydrochloride. Thus, in a preferred embodiment, the amount of thioridazine in a dosage unit delivers less than 150 mg of thioridazine per day. In more preferred embodiments, the composition of the invention comprises less than 10 mg of thioridazine, such as less than 8 mg such as comprising an amount of thioridazine or salts thereof equating less than 5 mg, such as less than 4 mg, such as less than 2 mg, such less than 1 mg, such as less than 0.5 mg, such as less than 0.25 mg of thioridazine, when used in combination with an antimicrobial agent. In the embodiment of the invention wherein the compound of formula I is thioridazine, the composition is administered orally, such that the composition of the invention comprising thioridazine and an antimicrobial agent is administered in the form of an oral solution, oral suspension, tablet or capsule.

In another preferred embodiment, the compound of formula I is chlorpromazine or salts or esters thereof. For its various uses, chlorpromazine is administered orally in dosage units of 10, 25, 50, 75, and 100 mg so as to provide a daily dose of 40 mg up to 1 g, depending on the indication. Thus, in a preferred embodiment, the amount of chlorpromazine in a dosage unit delivers less than 40 mg of chlorpromazine per day. In more preferred embodiments, the composition of the invention comprises less than 10 mg of chlorpromazine, such as less than 8 mg such as comprising an amount of chlorpromazine or salts thereof equating less than 5 mg, such as less than 4 mg, such as less than 2 mg, such less than 1 mg, such as less than 0.5 mg, such as less than 0.25 mg of chlorpromazine, when used in combination with an antimicrobial agent. In the embodiment of the invention wherein the compound of formula I is chlorpromazine, the composition is administered orally, such that the composition of the invention comprising chlorpromazine and an antimicrobial agent is administered in the form of an oral solution, oral suspension, tablet or capsule; or administered rectally in the form of a suppository; or administered parenterally such as by intramuscular injection.

In another preferred embodiment, the compound of formula I is perchlorperazine or salts or esters thereof. For its various uses, perchlorperazine is administered orally in dosage units as low as of 2.5 mg so as to provide a daily dose of 25 mg to about 100 mg depending on the indication. Thus, in a preferred embodiment, the amount of perchlorperazine in a dosage unit delivers less than 25 mg of perchlorperazine per day. In more preferred embodiments, the composition of the invention comprises less than 2.5 mg of perchlorperazine, such as less than 2 mg such as comprising an amount of perchlorperazine or salts thereof equating less than 1 mg, such as less than 0.5 mg, such as less than 0.25 mg of perchlorperazine, when used in combination with an antimicrobial agent. In the embodiment of the invention wherein the compound of formula I is perchlorperazine, the composition is administered orally, such that the composition of the invention comprising perchlorperazine and an antimicrobial agent is administered in the form of an oral solution, oral suspension, tablet or capsule; or administered rectally in the form of a suppository; or administered parenterally such as by intramuscular injection.

The composition comprising a compound of formula I and an antimicrobial agent is typically in the form of an oral solution, oral suspension, tablet or capsule.

The composition of the invention further comprises at least one antimicrobial agent, such as an antibiotic agent. Such antimicrobial agent may suitably be selected from beta-lactams, semisynthetic penicillin derivatives, clavulanic acid analogues, monobactams, carboxypenems, aminoglycosides, glycopeptides, lincomycins, macrolide antibiotics, polypeptides, polyenes, rifamycins, tetracyclines, semisynthetic tetracyclines, and chloramphenicol derivatives. Specific examples of such agents are well known to the skilled prescribing physician, or may be selected by aid of relevant pharmacopoeias or similar listings. For example, typical antimicrobials relevant within the context of treatment of resistant pathogens include, but are not limited to acyclovir, albendazole, amikacin, amphotericin B, aztreonam, azithromycin, caspofungin, cefepime, ceftriaxone, cefotaxime, chloramphenicol, cidofovir, clarithromycin, fluconazole, flucytosine, foscarnet, ganciclovir, imipenem, itraconazole, linezolid, meropenem, pentamidine, piperacillin-tazobactam, rifabutin, valganciclovir, vancomycin, penicillin, cephalosporin, griseofulvin, bacitracin, polymyxin B, erythromycin, neomycin, streptomycin, tetracycline, gentamicin, rifamycin, penicillin G, cephalothin, ampicillin, amoxycillin, clavamox, aztreonam, imipenem, streptomycin, gentamicin, clindamycin, polymyxin, bacitracin, amphotericin, nystatin, rifampicin, oxacillin, and doxycycline.

It should be understood that the compounds defined herein include possible salts thereof, of which pharmaceutically acceptable salts are especially relevant for the therapeutic applications. Salts include acid addition salts, which are particularly preferred, and basic salts. Examples of acid addition salts are hydrochloride salts, and addition salts with organic mono-, di-, or polycarboxylic acids such as fumarate, oxalate, tartrate, etc. Pharmaceutically acceptable salts may generally be selected from those described in Remington's *The Science and Practice of Pharmacy*, 20th Ed. Alfonso R. Gennaro (Ed.), Lippincott, Williams & Wilkins; ISBN: 0683306472, 2000, or in *Encyclopedia of Pharmaceutical Technology*, edited by Swarbrick, J. & J. C. Boylan, Marcel Dekker, Inc., New York, 1988. However, generally preferred salt forming agents for application in the present invention are organic mono- or dicarboxylic acids such as oxalic, fumaric, and maleic acid, and the like.

The antibiotic is typically selected from the group consisting of beta-lactams, semisynthetic penicillin derivatives, clavulanic acid analogues, monobactams, carboxypenems, aminoglycosides, glycopeptides, lincomycins, macrolide antibiotics, polypeptides, polyenes, rifamycins, tetracyclines, semisynthetic tetracyclines, and chloramphenicol derivatives. As stated, the invention allows for the use of lower amounts of antimicrobials such as antibiotics while effectively agent as bactericidal agents when combined with a phenothiazine. Typically, the antimicrobial may be present in an amount at least 10% less than the effective dose of the antimicrobial in the absence of the compound of formula I or in the absence of any other compound which reverses the resistance of microbe to said antimicrobial agent. More typically, the antimicrobial is present in an amount at least 10% less than the effective dose of the antimicrobial in the absence of the compound of formula I.

As stated, the synergistic effect is dramatic and the antimicrobial is more typically present in an amount of at least 15% less than the effective dose of the antimicrobial in the absence of the compound of formula I, such as at least 20% less, such as at least 25% less, such as at least 30% less, preferably at least 35% less, such as at least 40% less such as at least 45%, such as at least 50%.

As is known to the person skilled in the art, many bactericidal treatments require several fold dosage units throughout the day. Thus, alternatively stated, in the compositions of the in the invention, the microbial is present in an amount such that the daily dose of the antimicrobial is at least 10% less than the effective daily dose of the antimicrobial in the absence of the compound of formula I or in the absence of any other compound which reverses the resistance of microbe to said antimicrobial agent. Typically, the microbial is present in an amount such that the daily dose of the antimicrobial is at least 10% less than the effective daily dose of the antimicrobial in the absence of the compound of formula I. The antimicrobial is more typically present in an amount of at least 15% less than the effective dose of the antimicrobial in the absence of the compound of formula I, such as at least 20% less, such as at least 25% less, such as at least 30% less, preferably at least 35% less, such as at least 40% less such as at least 45%, such as at least 50%.

In one aspect of the invention the normal dosing regime of the antibiotic can be reduced by up to 10%; such as by up to 20%; such as by up to 30%; such as by up to 40%; such as by up to 50%; such as by up to 55%. Thus the dosing of an antibiotic in the present invention can be reduced, according to the dose provided by the MIC values exemplified in present invention.

In another aspect of the invention the risk of developing antibiotic resistance can be dramatically reduced. By combining the active principle of antibiotics with thioridazine, the effect of the antibiotic is increased up to 10 times giving two alternative advantages; the micro-organisms are up to 10 times as susceptible increasing the efficiency of the therapy; alternatively the therapeutic dose can be reduced concurrently with 90% while maintaining the therapeutic effect.

There is to be consensus in the field that MIC values can be used to calculate the relevant dose of the antibiotic. There is a general correlation between MIC and the prescribed dose; the prescribed dose will give a plasma level of 5 to 10 times the MIC value, assuming that the micro-organism has normal sensitivity towards the antibiotic.

As the person skilled in the art is aware, the sensitivity of a micro-organism towards an antibiotic can be expressed as the MIC value (Minimal Inhibitory Concentration). The MIC is defined as the lowest concentration of an antibiotic which will inhibit the (in vitro) growth of an infectious organism. Results are reported in micrograms per ml, as in the Examples. If an antibiotic acts bactericidal, the MBC value is the lowest concentration that will kill the micro-organism in question, also measured in microgram/mi. The MBC is defined as the lowest concentration of an antimicrobial agent needed to kill 99.9% of the initial organism inoculum.

The interpretation of in vitro data is based on achievable serum concentrations, which may vary depending on dose, route of administration, degree of protein binding, site of infection, age and weight of the patient, and other factors. As aware to the skilled person, the MIC value is a useful tool to estimate the needed plasma concentrations of the active principle as well as the relevant dose given to the patient. The time span in which the micro-organism is exposed to a concentration of the active principle above the MIC value is also of importance. Pharmacokinetic and pharmacodynamic properties of the active principle is of importance to the needed dosing. A useful tool for estimating the relevant dose can be calculating the Area Under the Curve (AUC) for 24 hours (mcgxhr/ml) and relate this value to MIC; $AUC_{24}$/MIC=AUIC. The ratio AUIC must preferably be more than 125. Having a AUIC>125 will ensure optimal antimicrobial effect.

As a general rule, the prescribed dose must give a plasma level of 2 to 10 times, such as 5 to 10 times the MIC value, given that the micro-organism has normal sensitivity towards the antibiotic. In micro-organisms that have already developed resistance to the antibiotic, this amount is 100 to 1000 times the MIC value.

In a combination of preferred embodiments, the compound of formula I is a phenothiazine derivative and the antimicrobial agent is an antibacterial agent selected from the group consisting of beta-lactams, cephalosporins and other beta lactams, cephems, penicillins and semisynthetic penicillin derivatives, clavulanic acid analogues, monobactams, carboxypenems, aminoglycosides, glycopeptides, lincomycins, macrolide antibiotics, polypeptides, polyenes, quinolones, rifamydns, tetracyclines, semisynthetic tetracyclines, antimycobacterials, and chloramphenicol derivatives and salts and esters thereof.

In a more typical embodiment, the an antibacterial agent is selected from the group consisting of beta-lactams, semisynthetic penicillin derivatives, clavulanic acid analogues, monobactams, carboxypenems, macrolide antibiotics, glycopeptides, tetracyclines, semisynthetic tetracyclines, and chloramphenicol derivatives, and salts and esters thereof. More typically, the antibacterial agent is selected from the group consisting of beta-lactams, semisynthetic penicillin derivatives, monobactams, carboxypenems, macrolide antibiotics and glycopeptides, preferably semisynthetic penicillin derivatives, macrolide antibiotics and glycopeptides.

In a suitable embodiment of the invention, the antibacterial agent is selected from the group consisting of erythromycin, oxacillin, vancomycin, and salts and derivatives thereof.

Erythromycin is conventionally administered in oral dose and amounts of the base, salt or ester thereof, expressed in terms of the base of 1-2 g in 2 to 4 divided doses. Dosage units in oral dosage form conventionally comprise an amount equating 250 mg or 500 mg of the base. In a suitable embodiment of the invention, the composition comprises a phenothiazine and an amount of erythromycin base, salt or ester equating 10-200 mg of erythromycin base, such as 10-175 mg, such as 10-150 mg, such as 10-125 mg, such as 10-100 mg. In an alternate embodiment, the composition comprises a phenothiazine and an amount of erythromycin base, salt or ester equating 15-200 mg of the erythromycin base, such as 20-200 mg, such as 50-200 mg, such as 75-200 mg.

Oxacillin, when administered orally as its sodium salt in an oral solution or capsule, is typically administered in dosage units of 500 mg to 1 g every 4 to 6 hours. In a suitable embodiment of the invention, the composition comprises a phenothiazine and oxacillin or salts thereof in an amount equating less than 500 mg of oxacillin, such as from 1-400 mg, such as from 1-350 mg, such as from 1-300 mg, such as from 1-250 mg, such as from 1-200 mg. In an alternate and suitable embodiment of the invention, the composition comprises a phenothiazine and an amount equating 1-350 mg of oxacillin, such as 5-350 mg, such as 10-350 mg, such as 50-350 mg, such as from 100-350 mg. In a further alternate embodiment, the composition comprises a phenothiazine and an amount equating 1-300 mg of oxacillin, such as 5-300 mg, such as 10-300 mg, such as 50-300 mg, such as from 100-300 mg.

The usual dose of Vancomycin is the equivalent of 500 mg of vancomycin every 6 hours or 1 g every 12 hours. In a suitable embodiment of the invention, the composition comprises a phenothiazine and Vancomycin or salts thereof in an amount equating less than 500 mg of Vancomycin, such as from 1-400 mg, such as from 1-350 mg, such as from 1-300 mg, such as from 1-250 mg, such as from 1-200 mg. In an alternate and suitable embodiment of the invention, the composition comprises a phenothiazine and an amount equating 1-350 mg of Vancomycin, such as 5-350 mg, such as 10-350 mg, such as 50-350 mg, such as from 100-350 mg. In a further alternate embodiment, the composition comprises a phenothiazine and an amount equating 1-300 mg of Vancomycin, such as 5-300 mg, such as 10-300 mg, such as 50-300 mg, such as from 100-300 mg.

The above doses are those intended for adult patients. Dosage units intended for infants would be 10-60% of the above amounts, applicable over every range.

A further aspect of the invention relates to the use of a composition comprising a compound of formula I for the preparation of a medicament for the treatment of a patient with a microbial infection. In a suitable embodiment, the patient is infected with a bacteria which has at least some or some degree of antibacterial resistance. In a typical embodiment of this aspect of the invention, the composition further comprises an antibiotic. The composition in this aspect of the invention may be as defined supra.

Due to issues of formulation, in an aspect of the invention, the phenothiazine and antimicrobial agent are not administered in a singular dosage unit but are each instead in separate dosage units. The dosage units are preferably administered simultaneously but may be administered in a non-simultaneous fashion due to differential absorption at the either fast or fed state of the antimicrobial agent and compound of the formula I. One aspect of the invention defines a kit comprising a first dosage unit comprising a compound of formula I and a further dosage unit comprising an antibacterial agent. In the kit, the antibacterial agent is typically selected from the group consisting of beta-lactams, semisynthetic penicillin derivatives, clavulanic acid analogues, monobactams, carboxypenems, aminoglycosides, glycopeptides, lincomycins, macrolide antibiotics, polypeptides, polyenes, rifamycins, tetracyclines, semisynthetic tetracyclines, and chloramphenicol derivatives. In the kit, the compound of formula I is typically a phenothiazine derivative. In the kit of the invention, the phenothiazine derivative is typically selected from the group consisting of (±)thioridazine, (+)thioridazine, (−)-thioridazine, chlorpromazine, and perchlorperazine, and salts thereof.

A further aspect of the invention relates to a method of treating an bacterial infection comprising administering a composition, as defined in any one claim 1-26.

A further aspect of the invention relates to a method for the prophylactic or curative treatment of an infection associated with at least one microbe or microbial strain displaying at least some degree of antimicrobial resistance comprising administering to a subject a composition as defined in any one of claims 1-26. In this aspect of the invention, the method typically comprises least one antimicrobial agent in a dosage amount at least 10% less than the effective unit dose of said antibacterial. More typically, the antimicrobial is in an amount such that the daily dose of the antimicrobial is at least 10% less than the effective daily dose of the antimicrobial in the absence of the compound of formula I. Even more typically, the antimicrobial is in an amount such that the daily dose of the antimicrobial is at least 15% less than the effective dose of the antimicrobial in the absence of the compound of formula I, such as at least 20% less, such as at least 25% less, such as at least 30% less, preferably at least 35% less, such as at least 40% less such as at least 45%, such as at least 50%.

In a further aspect, the present invention provides a composition comprising an antimicrobial and a compound of formula IIA, substantially free from its epimer, or a pharmaceutically acceptable salt thereof, and a pharmaceutically acceptable excipient or

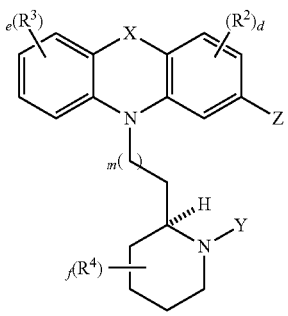

IIA carrier.

In a further aspect, the present invention provides a composition comprising an antimicrobial agent and compound of formula IIB, substantially free from its epimer, or a pharmaceutically acceptable salt thereof, and a pharmaceutically acceptable excipient or carrier.

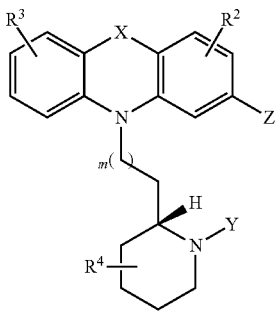

IIB

The compounds of generic formulae IIA and IIB, being stereoisomers, may be described by common definitions of the variable groups, namely:

X may be selected from the group comprising O, $NR^1$, Se, P, PO, SO and S;

Z may be selected from the group comprising $SR^5$, $SOR^5$, $SO_2R^5$, $NHR^5$, $NR^5R^5$, $NR^1R^5$, $OR^5$, $COR^5$, $COOR^5$, and $POR^5$, $PO_2R^5$, $PO_2OR^5$, and $OPO_2OR^5$;

Y may be hydrogen or $C_{1-6}$-alkyl;

m is a whole number selected from the group consisting of 0, 1, 2, 3, 4, 5, and 6;

$R^1$ may be selected from the group comprising hydrogen, $C_{1-6}$-alkyl, $C_{3-8}$-cycloalkyl, aryl, heteroaryl, arylalkyl, heteroarylalkyl, CO—$C_{1-6}$-alkyl, CO—$C_{3-8}$-cycloalkyl, COO—$C_{1-6}$-alkyl, COO—$C_{3-8}$-cycloalkyl, CO-aryl, CO-heteroaryl, COO-aryl, COO-heteroaryl, arylalkyl-CO, heteroarylalkyl-CO, arylalkyl-OOC and heteroarylalkyl-OOC;

Each $R^2$ may independently be selected from the group comprising $C_{1-6}$-alkyl, halogen, $C_{3-8}$-cycloalkyl, OH, $NH_2$, $NHR_1$, $N(R_1)_2$, O—$C_{1-6}$-alkyl, O—$C_{3-8}$-cycloalkyl, NH—$C_{1-6}$-alkyl, NH—$C_{3-8}$-cycloalkyl, S—$C_{1-6}$-alkyl, S—$C_{3-8}$-cycloalkyl, aryl, heteroaryl, aryloxy, heteroaryloxy, arylamino, heteroarylamino, arylalkyl, heteroarylalkyl, arylalkyloxy and heteroarylalkyloxy;

d is selected from 0, 1, 2, and 3;

Each $R^3$ may independently be selected from the group comprising $C_{1-6}$-alkyl, halogen, $C_{3-8}$-cycloalkyl, OH, $NH_2$, $NHR_1$, $N(R_1)_2$, O—$C_{1-6}$-alkyl, O—$C_{3-8}$-cycloalkyl, NH—$C_{1-6}$-alkyl, NH—$C_{3-8}$-cycloalkyl, S—$C_{1-6}$-alkyl, S—$C_{3-8}$-cycloalkyl, aryl, heteroaryl, aryloxy, heteroaryloxy, arylamino, heteroarylamino, arylalkyl, heteroarylalkyl, arylalkyloxy and heteroarylalkyloxy;

e is selected from 0, 1, 2, 3, and 4;

Each $R^4$ may independently be selected from the group comprising $C_{1-6}$-alkyl, halogen, $C_{3-8}$-cycloalkyl, OH, O—$C_{1-6}$-alkyl, O—$C_{3-8}$-cycloalkyl, aryl, heteroaryl, aryloxy, heteroaryloxy, arylalkyl, heteroarylalkyl, arylalkyloxy and heteroarylalkyloxy;

f is selected from 0, 1, 2, 3, 4, 5, 6, 7, and 8; and $R^5$ may be selected from the group comprising hydrogen, $C_{1-6}$-alkyl, $C_{3-8}$-cycloalkyl, aryl, heteroaryl, arylalkyl, and heteroarylalkyl.

Preferred embodiments of the compounds and compositions of the invention are those comprising compounds of general formulae I or II wherein:

X is selected from O, $NR^1$, SO and S, especially from $NR^1$ and S, and

Z is selected from $SR^5$, $SOR^5$, $SO_2R^5$, $NHR_5$, $NR^5R^5$, $NR^1R^5$, and $OR^5$, especially from $SR^5$, $SOR^5$, $SO_2R^5$, and Y is $C_{1-6}$-alkyl, such as $C_{1-3}$-alkyl, with methyl being most preferred, and m is 1, 2, or 3, such as 1 or 2, with 1 being most preferred, and $R^1$ is hydrogen, $C_{1-6}$-alkyl, $C_{3-8}$-cycloalkyl, aryl, heteroaryl, arylalkyl, or heteroarylalkyl, wherein hydrogen, $C_{1-6}$-alkyl, and $C_{3-8}$-cycloalkyl, especially hydrogen or $C_{1-6}$-alkyl are most preferred, and Each $R^2$ is independently $C_{1-6}$-alkyl, halogen, $C_{3-8}$-cycloalkyl, OH, $NH_2$, $NHR_1$, $N(R_1)_2$, O—$C_{1-6}$-alkyl, O—$C_{3-8}$-cycloalkyl, S—$C_{1-6}$-alkyl, or S—$C_{3-8}$-cycloalkyl, with $C_{1-6}$-alkyl, halogen, or O—$C_{1-6}$-alkyl being especially suitable, and d is 0, 1, or 2, more preferably 0 or 1, such as 0, and Each $R^3$ is independently $C_{1-6}$-alkyl, halogen, $C_{3-8}$-cycloalkyl, OH, $NH_2$, $NHR_1$, $N(R_1)_2$, O—$C_{1-6}$-alkyl, O—$C_{3-8}$-cycloalkyl, S—$C_{1-6}$-alkyl, or S—$C_{3-8}$-cycloalkyl, with $C_{1-6}$-alkyl, halogen, or O—$C_{1-6}$-alkyl being especially suitable, and e is 0, 1, 2, or 3, more preferably 0, 1, or 2, such as 0 or 1, and Each $R^4$ is independently $C_{1-6}$-alkyl, halogen, $C_{3-8}$-cycloalkyl, OH, O—$C_{1-6}$-alkyl, or O—$C_{3-8}$-cycloalkyl, more preferably $C_{1-6}$-alkyl, halogen, or O—$C_{1-6}$-alkyl, with $C_{1-6}$-alkyl or halogen being especially suitable, and f is 0, 1, 2, 3, or 4, more preferably 0, 1, 2, or 3, typically 0, 1, or 2, such as 0 or 1, and $R^5$ is hydrogen, $C_{1-6}$-alkyl, or $C_{3-8}$-cycloalkyl, suitably $C_{1-6}$-alkyl or $C_{3-8}$-cycloalkyl, most preferably $C_{1-6}$-alkyl, such as methyl, ethyl, propyl or isopropyl.

A further embodiment of this aspect of the invention relates to a composition comprising a compound of formula IIA or IIB and further comprising an agent selected from the group consisting of anti-fungal agent, an anti-viral agent, an anti-bacterial agent, and an anti-parasitic agent.

The present invention further relates to compositions comprising enantiomerically enriched compounds of formulae IIA or IIB. While any optically active sample of a compound of formula IIA or IIB may be accommodated by this description, it is generally suitable that the compound is substantially free from its epimer, as defined by the formulae. More specifically, typical compositions of the invention comprise compounds of formula IIA or IIB substantially free from the epimeric form arising because of the stereogenic center located at the 2-position of the piperidine moiety, and it is generally preferred that the compositions are made up from a compound of formula I or II containing at most 20%, preferably at most 10%, more preferably at most 5%, most preferably at most 2.5%, such as at most or less than 1% of its epimer.

A particularly suitable composition of the present invention comprises (S)-thioridazine or a pharmaceutically acceptable salt thereof, an antimicrobial agent, and a pharmaceutically acceptable carrier. Alternatively, this particular composition may be defined as comprising predominantly the levorotatory enantiomer of thioridazine. More precisely, this composition preferentially contains at most 20%, preferably at most 10%, more preferably at most 5%, most preferably at most 2.5%, such as less than 1% of the dextrorotatory enantiomer.

Another particular composition of the present invention comprises (R)-thioridazine or a pharmaceutically acceptable salt thereof, an antimicrobial agent, and a pharmaceutically acceptable carrier. Alternatively, this particular composition may be defined as comprising predominantly the dextrorotatory enantiomer of thioridazine. More precisely, this composition preferentially contains at most 20%, preferably at most 10%, more preferably at most 5%, most preferably at most 2.5%, such as less than 1% of the levorotatory enantiomer.

In a further aspect, the present invention relates to the use of a compound of formula IIA or IIB, as defined above, for the preparation of a medicament for the therapeutic or prophylactic treatment of a patient diagnosed with an infection associated with at least one microbe which displays at least some degree of antimicrobial resistance, or otherwise deemed to potentially benefit from such treatment.

A related aspect of the invention relates to the use of a compound of formula IIA or IIB for the preparation of a medicament for the treatment of antimicrobial-resistant infections. The invention is furthermore directed to the use of a compound of formula IIA or IIB for the preparation of a medicament for the treatment of antimicrobial-resistant infections. As stated, the anti-microbial resistant infection is preferably anti-bacterial resistant infection.

The administration route of the compositions as defined herein may be any suitable route which leads to a concentration in the blood or tissue corresponding to a therapeutic concentration. Thus, e.g., the following administration routes may be applicable although the invention is not limited thereto: the oral route, the parenteral route, the cutaneous route, the nasal route, the rectal route, the vaginal route and the ocular route. It should be clear to a person skilled in the art that the administration route is dependent on the particular condition in question, and that a variety of pharmaceutically acceptable excipients and/or carriers may be useful for preparing the compositions of the invention.

The compounds as defined herein may be contained in any appropriate amount in the pharmaceutical composition, and are generally contained in an amount of about 1-95% by weight of the total weight of the composition. The composition may be presented in a dosage, such as a unit dosage form, which is suitable for the oral, parenteral, rectal, cutaneous, nasal, vaginal and/or ocular administration route. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, aerosols and in other suitable form.

Pharmaceutical compositions according to the present invention may be formulated to release the active compound substantially immediately upon administration or at any substantially predetermined time or time period after administration. The latter type of compositions are generally known as controlled release formulations.

In the present context, the term "controlled release formulation" embraces i) formulations which create a substantially constant concentration of the drug within the body over an extended period of time, ii) formulations which after a predetermined lag time create a substantially constant concentration of the drug within the body over an extended period of time, iii) formulations which sustain drug action during a predetermined time period by maintaining a relatively, constant, effective drug level in the body with concomitant minimization of undesirable side effects associated with fluctuations in the plasma level of the active drug substance (sawtooth kinetic pattern), iv) formulations which attempt to localize drug action by, e.g., spatial placement of a controlled release composition adjacent to or in the diseased tissue or organ, v) formulations which attempt to target drug action by using carriers or chemical derivatives to deliver the drug to a particular target cell type.

Controlled release formulations may also be denoted "sustained release", "prolonged release", "programmed release", "time release", "rate-controlled" and/or "targeted release" formulations.

Controlled release pharmaceutical compositions may be presented in any suitable dosage forms, especially in dosage forms intended for oral, parenteral, cutaneous nasal, rectal, vaginal and/or ocular administration. Examples include single or multiple unit tablet or capsule compositions, oil solutions, suspensions, emulsions, microcapsules, microspheres, nanoparticles, liposomes, delivery devices such as those intended for oral, parenteral, cutaneous, nasal, vaginal or ocular use.

The compositions of the present invention may be administered in an amount of about 1-1000 mg active ingredient per kg body weight per day, such as about 5-500 mg per kg body weight per day.

For compositions adapted for rectal use for preventing diseases, a somewhat higher amount of the compound is usually preferred, i.e. from approximately 1 mg to 100 mg per kg body weight per day.

For parenteral administration, a dose of about 0.1 mg to about 50 mg per kg body weight per day is convenient. For intravenous administration a dose of about 0.1 mg to about 20 mg per kg body weight per day administered for 1 day to 3 months is convenient. For intraarticular administration a dose of about 0.1 mg to about 20 mg per kg body weight per day is usually preferable. For parenteral administration in general, a solution in an aqueous medium of 0.5-2% or more of the active ingredients may be employed.

For topical administration on the skin, a dose of about 1 mg to about 5 g administered 1-10 times daily for 1 week to 12 months is usually preferable. drugs.

The compounds I, IIA and IIB of the invention may be prepared according to procedures known in the prior art. Preparation of the compounds in optically active form may also be achieved by known methods. Relevant citations are Patrick et al. *Chirality* 1991, 3, 208, GB 873,316, Bourquin et al. *Helv. Chim. Acta* 1958, 41, 1072, which are hereby included by reference. Generally, the synthesis of compounds of formula I and II may be accomplished by alkylation of an appropriately substituted phenothiazine derivative with an enantiomerically enriched alkylene derivative possessing the 2-piperidinyl moiety at one terminus and a suitable nucleofuge, such as a halogen, at the other.

The invention is further demonstrated by the non-limiting Examples.

EXAMPLES

Example 1

**In Vitro Activity of Phenothiazine Derivatives in *Enterococcus faecalis* and *Enterococcus faecium***

The antimicrobial activity of the phenothiazine derivatives thioridazine and prochlorperazine have been evaluated with 11 *Enterococcus faecalis* strains and 9 *Enterococcus faecium* strains, originating from human infections and animal fecal flora.

The present inventors found that all *E. faecalis* and *E. faecium* strains, regardless of their susceptibility to commonly used antibiotics, were inhibited by thioridazine at a concentration of 16-32 µg/ml and by prochlorperazine at a concentration of 32-64 µg/ml. Combinations of the antibiotics vancomycin or ampicillin and thioridazine and prochlorperazine at subinhibitory concentrations, render vancomycin or ampicillin resistant bacteria sensitive to each of the antibiotics. Verapamil and reserpine, inhibitor of P-glycoprotein-mediated multidrug resistance, did not reduce resistance. The results outline modification of resistance in enterococci induced by phenothiazine derivatives unrelated to P-glycoprotein-mediated multidrug resistance.

The aim of the present example is to demonstrate the combined effect of antibiotics and resistance modifiers (different phenothiazine derivatives) on human isolates of *E. faecalis* strains and to establish, which combination of antibiotic/antimicrobial agent could perform modification of resistance on the bacterial samples. As enterococci do posses multidrug resistance (ABC) efflux pumps, the present inventors demonstrates the possibility to reciprocate the observed effect by utilising the known efflux pump inhibitors verapamil and reserpine.

Materials and Methods

Reagents were purchased from reputable and conventional providers

Bacterial Strains

Strains of *E. faecalis* and *E. faecium* were clinical isolates obtained from Sønderborg, Odense and Statens Serum Institut (SSI), Copenhagen, Denmark. According to the profile of vancomycin-resistance, tested strains were either vancomycin-sensitive, VanA- or VanB-positive enterococci. Resistance determination was performed in accordance to the National Committee for Clinical Laboratory Standards (NCCLS) and national guidelines (SSI).

Animal Strains

Animal strains were isolated from the feces of pigs and poultry in Belgium and Denmark and donated by the Veterinary and Agrochemical Research Center (VAR), Brussels, Belgium and the Danish Veterinary Laboratory, Copenhagen, Denmark.

Culture Media

Oxoid Iso-Sensitest agar was purchased from Oxoid, and adjusted to pH 7.3.

Tryptic Soy broth was purchased from Fluka, Buchs, Switzerland and adjusted to pH 7.3.

MIC Determinations

The minimum inhibitory concentration (MIC) of each antibiotic against various strains employed in this study was determined by the E-test system (Sanchez et al. 1992) and checkerboard microdilution techniques (Eliopulos & Moellering 1991).

MICs for test substances thioridazine, prochlorperazine were determined by agar-dilution (Ericsson & Sherris 1971) and with microdilution technique as well. Thioridazine and prochlorperazine were added to the plates at concentrations from 0.5-256 µg/ml in order to identify MICs for testsubstances.

Combinations of subinhibitory concentrations of testsubstances (4-12 µg/ml) and standardized concentrations of vancomycin and ampicillin (1-64 µg/ml) were added to the plates in order to investigate the influence of the testsubstances on the MIC values against susceptible and resistant bacterial strains. MIC-measurements were done three times. All tests were performed at pH 7.3 in order to create optimal growth circumstances. The interaction of each antibiotic with the test substances thioridazine and prochlorperazine and the efflux inhibitors verapamil and reserpine was determined by the checkerboard method and interpretation of synergy, additive or interference effects obtained as prescribed.

Results

The sensitivity of enterococcal strains to either ampicillin or vancomycin by the E-test is presented in Table 1. The interpretation of clinical susceptibility/resistance is also presented. The sensitivity of the strains to thioridazine and prochlorperazine is presented in Table 2. Comparing these data to that of Table 1 suggests that the sensitivity to these agents is more consistent than that for the antibiotics. The checkerboard method show the interaction of two distinct agents each at concentrations below their MIC and the resulting activity on a given bacterial strain. Accordingly, as shown by Table 3, varying combinations of ampicillin or vancomycin with thioridazine or prochlorperazine against most of the strains isolated from humans, with two exceptions, inhibited the growth of the strains tested with concentrations of either agent well below their MIC. This inhibitory effect was either minimal (additive) or significantly expressed (synergistic). The combinations of ampicillin and prochlorperazine against strain A as well as vancomycin and thioridazine against Strain B yielded no additional effect and these were the two exceptions noted. Comparison of the data of Table 3 to that of Table 1 or 2 do not yield any correlation between the degree of interaction and the sensitivity of the strain to either the antibiotic or the phenothiazine. Combinations of the tested antibiotics with either reserpine or verapamil did not show any influence on the MIC-values, thus resulting in no further enhancement of the effect of each combination.

Discussion

The present experiment shows that phenothiazine derivates, especially thioridazine have an antimicrobial effect against the investigated strains *E. faecalis* and *E. faecium* regardless of preexisting resistance patterns or origin (human, veterinary). This was also demonstrated for *S. aureus* and compounds chlorpromazine and thioridazine (Kaatz et al. 2003).

Furthermore, it could be shown that the β-lactam ampicillin as well as vancomycin MIC's can be lowered when combined with the test-substances at subinhibitory concentrations. The MIC reduction was observed both with the agardilution method and by the microdilution method. Significant results were achieved by performing these to different methods and demonstrated synergism between the used antibiotics and non-antibiotics. According to the observed synergistic effect of antibiotics and non-antibiotics different aspects of this interaction have to be discussed:

Since verapamil and reserpine do not influence the MIC's of the antibiotics, it can be assumed that P-glycoprotein-mediated MDR efflux is not the mechanism of resistance influenced by our test compounds. Since the activity of the non-antibiotic is independent of the preexisting resistance pattern, the targets of the investigated antibiotics and non-antibiotics are probably different. Phenothiazines do reduce the level of beta-lactam resistance in both staphylococci and enterococci.

TABLE 1

Resistance patterns of enterococcal strains to either ampicillin or vancomycin by the E-test are presented. The interpretation of clinical susceptibility/resistance from these data is also presented.

|  | MIC of ampicillin (mg/l) | Interpretation | MIC of vancomycin (mg/l) | Interpretation |
|---|---|---|---|---|
| Human *E. faecalis* strains | | | | |
| A | 0.5 | S | 48 (Van B) | R |
| B | 0.5 | S | 4 (Van B) | R |
| C | 1 | S | 32 (Van B) | R |
| D | 1 | S | >256 (Van A) | R |
| E | 32 | R | 2 | S |
| Human *E. faecium* strains | | | | |
| 87156 | 48 | R | 2 | S |
| 73047, 91185 | 48 | R | 3 | S |
| 76366 | >256 | R | 3 | S |
| 79765 | 24 | R | 3 | S |
| Veterinary *E. faecalis* strains | | | | |
| VT16, VT 22, DR 2891 | 1 | S | 6 | R |
| VT 37 | 1 | S | 4 | R |
| VT 71 | 2 | S | 4 | R |

TABLE 1-continued

Resistance patterns of enterococcal strains to either ampicillin or vancomycin by the E-test are presented. The interpretation of clinical susceptibility/resistance from these data is also presented.

|  | MIC of ampicillin (mg/l) | Interpretation | MIC of vancomycin (mg/l) | Interpretation |
|---|---|---|---|---|
| DR 2698 | 1 | S | 2 | S |
| Veterinary *E. faecium* strains | | | | |
| 30651 | 8 | R | 1.5 | S |
| 30656, 30665 | 6 | R | 1.5 | S |
| 30658 | 4 | R | 1.5 | S |

Legend:
1. MIC: Minimal Inhibition Concentration defined in milligram per litre (mg/l)
2. State of sensitivity: S: sensitive R: resistant

TABLE 2

Sensitivity of enterococcal strains to the used resistance modifiers thioridazine (THIO) and prochlorperazine (PCP) determined by agar dilution is presented.

|  | MIC of THIO (mg/l) | MIC of PCP (mg/l) |
|---|---|---|
| Human *E. faecalis* strains | | |
| A, B, C, D, E | 16 | 64 |
| Human *E. faecium* strains | | |
| 73047 | 16 | 32 |
| 76366, 79765, 87156, 91185 | 16 | 64 |
| Veterinary *E. faecalis* strains | | |
| VT 16, VT 22, VT 37, VT 71 DR 2698, DR 2891 | 16 | 32 |
| Veterinary *E. faecium* strains | | |
| 30651, 30656, 30665, | 16 | 64 |
| 30658 | 16 | 32 |

Legend:
1. MIC: Minimal Inhibition Concentration defined in milligram per liter (mg/l)
2. Phenothiazines: THIO: Thioridazine & PCP: Prochlorperazine

TABLE 3

Presentation of MIC values and summarized interpretatation of the mode of activity observed for human *Enterococcus faecalis* in the microdilution checkerboard is presented.

| Strain | Antibiotic (MIC μg/ml) | Resistance modifier (MIC μg/ml) | Combination of drugs (MIC μg/ml) | Mode of activity |
|---|---|---|---|---|
| A | AMP (32) | THIO (32) | AMP (1) + THIO (16) | Additive plus |
|  |  | PCP (32) | AMP (32) + PCP (0.25) | — |
|  | VAN (192) | THIO (32) | VAN (6) + THIO (8) | Synergy |
|  |  | PCP (32) | VAN (48) + PCP (16) | Additive plus |
| B | AMP (2) | THIO (32) | AMP (0.5) + THIO (8) | Synergy |
|  |  | PCP (64) | AMP (0.5) + PCP (16) | Synergy |
|  | VAN (4) | THIO (32) | VAN (2) + THIO (32) |  |
|  |  | PCP (64) | VAN (1) + PCP (16) | Additive plus |

TABLE 3-continued

Presentation of MIC values and summarized interpretatation
of the mode of activity observed for human *Enterococcus faecalis*
in the microdilution checkerboard is presented.

| Strain | Antibiotic (MIC µg/ml) | Resistancemodifier (MIC µg/ml) | Combination of drugs (MIC µg/ml) | Mode of activity |
|---|---|---|---|---|
| C | AMP (16) | THIO (32) | AMP (4) + THIO (4) | Synergy |
|   |          | PCP (32)  | AMP (8) + PCP (0.5) | Additive plus |
|   | VAN (128)| THIO (32) | VAN (64) + THIO (4) | Additive plus |
|   |          | PCP (32)  | VAN (64) + PCP (8) | Additive plus |
| D | AMP (1)  | THIO (32) | AMP (0.25) + THIO (4) | Synergy |
|   |          | PCP (32)  | AMP (0.25) + PCP (8) | Synergy |
|   | VAN (500)| THIO (32) | VAN (32) + THIO (8) | Synergy |
|   |          | PCP (32)  | VAN (32) + PCP (8) | Synergy |
| E | AMP (128)| THIO (32) | AMP (16) + THIO (8) | Synergy |
|   |          | PCP (32)  | AMP (64) + PCP (16) | Additive plus |
|   | VAN (2)  | THIO (32) | VAN (1) + THIO (2) | Additive plus |
|   |          | PCP (32)  | VAN (0.5) + PCP (8) | Synergy |

Legend:
1. Antibiotics: AMP: Ampicillin & VAN: Vancomycin
2. Phenothiazines: THIO: Thioridazines & PCP: Prochlorperazine

REFERENCES

GB 873,316
Akiyama et al. *JNCI* 1986, 76, 839
De Gaitani et al. *Chirality* 2003, 15, 479
Eap et al. *J. Chromatog. B: Biomed. Appl.* 1995, 669, 271
Kaatz G. W., V. V. Mougdal, S. M. Seo, and J. E. Kristiansen, Phnothiazines and Thioanthenes inhibit Multidrug Efflux Pump activity in *Staphylococcus aureus*. Antimicrob. Agents. Chemother. 2003, 47, 719-726.
Kristiansen, M., 5*th European Congress on Chemotherapy and Infection*, Rhodes, 2003
Ordway et al. *Antimicrobial Agents Chemother.* 2003, 47, 917
Patrick et al. *Chirality* 1991, 3, 208
Radhakrishnan et al. *Indian J. Exp. Biol.* 1999, 37, 671
Ramu et al. *Cancer Chemother. Pharmacol.* 1992, 30, 165
Svendsen et al. *Psychiatry Research* 1988, 23, 1
Svendsen et al. *Neuropharmacol.* 1988, 27, 1117-25
Remington's *The Science and Practice of Pharmacy*, 20th Ed. Alfonso R. Gennaro (Ed.), Lippincott, Williams & Wilkins; ISBN: 0683306472, 2000
*Encyclopedia of Pharmaceutical Technology*, edited by Swarbrick, J. & J. C. Boylan, Marcel Dekker, Inc., New York, 1988

The invention claimed is:

1. A pharmaceutical composition presented in a dosage comprising an antimicrobial agent and an amount of (−)-thioridazine or a pharmaceutically acceptable salt thereof that delivers less than 150 mg per day of the (−)-thioridazine or a pharmaceutically acceptable salt thereof and further comprising a pharmaceutically acceptable excipient or carrier, wherein the composition comprises at most 20% of dextrorotary epimer of thioridazine, or a salt thereof.

2. The composition according to claim 1, wherein the antimicrobial agent is an antibiotic selected from the group consisting of bata-lactams, semisynthetic penicillin derivatives, clavulanic acid analogues, monobactams, carboxypenems, aminoglycosides, glycopeptides, lincomycins, macrolide antibiotics, polypeptides, polyenes, rifamycins, tetracyclines, semisynthetic tetracyclines, and chloramphenicol derivatives.

3. The composition according to claim 1, wherein the antimicrobial agent is present in an amount at least 10% less than the effective dose of the antimicrobial agent in the absence of the (−)-thioridazine or in the absence of any other compound which reverses the resistance of microbe to said antimicrobial agent.

4. The composition according to claim 1, wherein the antimicrobial agent is present in an amount at least 10% less that the effective dose of the antimicrobial agent in the absence of the (−)-thioridazine.

5. The composition according to claim 1, wherein the antimicrobial agent is present in an amount of at least 15% less than the effective dose of the antimicrobial agent in the absence of the (−)-thioridazine.

6. The composition according to claim 1, wherein the antimicrobial agent is present in an amount such that the daily dose of the antimicrobial is at least 10% less than the effective daily dose of the antimicrobial agent in the absence of the (−)-thioridazine or in the absence of any other compound which reverses the resistance of microbe to said antimicrobial agent.

7. The composition according to claim 1, wherein the antimicrobial agent is present in an amount such that the daily dose of the antimicrobial agent is at least 10% less than the effective daily dose of the antimicrobial agent in the absence of the (−)-thioridazine.

8. The composition according to claim 6, wherein the antimicrobial agent is present in an amount of at least 15% less than the effective dose of the antimicrobial agent in absence of the (−)-thioridazine.

9. The composition according to claim 1, wherein the antimicrobial agent is an antibacterial agent selected from the group consisting of bata-lactams, penicillins and semisynthetic penicillin derivatives, clavulanic acid analogues, monobactams, carboxypenems, aminoglycosides, glycopeptides, lincomycins, macrolide antibiotics, polypeptides, polyenes, quinolones, rifamycins, tetracyclines, semisynthetic tetracyclines, antimicrobials, and chloramphenicol derivatives.

10. The composition according to claim 9, wherein the antibacterial agent is selected from the group consisting of bata-lactams, semisynthetic penicillin derivatives, clavulanic acid analogues, monobactams, carboxypenems, macrolide antibiotics, glycopeptides, tetracyclines, semisynthetic tetracyclines, and chloramphenicol derivatives.

11. The composition according to claim 10, wherein the antibacterial agent is selected from the group consisting of beta-lactams, semisynthetic penicillin derivatives, monobactams, carboxypenems, macrolide antibiotics and glycopeptides, preferably semisynthetic penicillin derivatives, macrolide antibiotics and glycopeptides.

12. The composition according to claim 11, wherein the antibacterial agent is selected from the group consisting of erythromycin, oxacillin vancomycin, and salts and derivatives thereof.

13. A composition comprising an antimicrobial agent and the levorotatory enantiomer of thioridazine, or a salt thereof.

* * * * *